(12) United States Patent
Lee et al.

(10) Patent No.: US 7,220,861 B2
(45) Date of Patent: May 22, 2007

(54) PROCESSES FOR PREPARING QUINOLONECARBOXYLATE DERIVATIVES

(75) Inventors: Tai Au Lee, Seoul (KR); Nam Jin Park, Suwon (KR); Ja Heouk Khoo, Kumpo (KR); Seong Ho Song, Seoul (KR); Ju Young An, Seoul (KR)

(73) Assignee: Yuhan Corporation, Seoul (KR)

( * ) Notice: Subject to any disclaimer, the term of this patent is extended or adjusted under 35 U.S.C. 154(b) by 126 days.

(21) Appl. No.: 10/537,945

(22) PCT Filed: Dec. 19, 2003

(86) PCT No.: PCT/KR03/02785

§ 371 (c)(1),
(2), (4) Date: Jun. 9, 2005

(87) PCT Pub. No.: WO2004/056781

PCT Pub. Date: Jul. 8, 2004

(65) Prior Publication Data

US 2006/0058528 A1      Mar. 16, 2006

(30) Foreign Application Priority Data

Dec. 21, 2002   (KR)   ................ 10-2002-0082222

(51) Int. Cl.
C07D 215/56   (2006.01)
C07D 498/06   (2006.01)
(52) U.S. Cl. .................... 546/156; 546/155; 544/101
(58) Field of Classification Search ............. 546/156, 546/155; 544/101
See application file for complete search history.

(56) References Cited

U.S. PATENT DOCUMENTS

| 4,599,334 A | 7/1986 | Petersen et al. |
| 4,730,000 A | 3/1988 | Chu |
| 4,762,844 A | 8/1988 | Grohe et al. |
| 4,777,253 A | 10/1988 | Mitscher et al. |
| 4,795,751 A | 1/1989 | Masumoto et al. |
| 4,880,806 A * | 11/1989 | Ueda et al. .................. 514/249 |
| 4,977,263 A | 12/1990 | Schriewer et al. |
| 5,182,401 A * | 1/1993 | Grohe ......................... 546/287 |
| 5,237,060 A | 8/1993 | Schriewer et al. |
| 5,407,932 A | 4/1995 | Kuramoto et al. |
| 5,639,886 A | 6/1997 | Zerbes et al. |
| 5,869,661 A | 2/1999 | Ochi et al. |
| 6,316,618 B1 * | 11/2001 | Park et al. ................... 544/101 |
| 6,699,992 B2 * | 3/2004 | Wang et al. ................. 546/156 |
| 2002/0120138 A1 | 8/2002 | Lui et al. |

FOREIGN PATENT DOCUMENTS

| JP | 1-100165 | 4/1989 |
| WO | WO 00/50428 | 8/2000 |

OTHER PUBLICATIONS

Organicum, 3$^{rd}$ edition, 1964, p. 438 (cited in US 4,977,263).
J. Med. Chem., 1989, 32, pp. 1313-1318.
J. Med. Chem., 1986, 29, pp. 2363-2369.
J. Org. Chem., 1970, 35, pp. 930-935.

* cited by examiner

*Primary Examiner*—D. Margaret Seaman
(74) *Attorney, Agent, or Firm*—Lowe Hauptman & Berner, LLP.

(57) ABSTRACT

Provided is a process for preparing quinolonecarboxylate derivatives under a mild condition in high yield, so as to be favorably applied to a large-scale mass production thereof.

9 Claims, No Drawings

PROCESSES FOR PREPARING QUINOLONECARBOXYLATE DERIVATIVES

The present application is based on International Application No. PCT/KR/2003/002785 filed Dec. 19, 2003, and claims priority from, Korean Application Number 10-2002-0082222 filed Dec. 21, 2002, the disclosure of which is hereby incorporated by reference herein in its entirety.

BACKGROUND OF THE INVENTION

1. Field of the Invention

The present invention relates to a process for preparing quinolonecarboxylate derivatives, which are useful as an intermediate for the preparation of quinolone anti-bacterial agents.

2. Description of the Related Art

Quinolonecarboxylate derivatives are useful as an intermediate for the preparation of various quinolone anti-bacterial agents, including sparfloxacin, gemifloxacin, trovafloxacin, ciprofloxacin, temafloxacin, fleroxacin, and levofloxacin.

Conventional processes for preparing quinolonecarboxylate derivatives includes a quinoline-ring forming step (i.e., cyclization step), which is performed in the presence of a base such as potassium carbonate or sodium hydride (see U.S. Pat. No. 5,639,886; *J. Med. Chem.*, 1989, 32,1313–1318; WO 00/50428; U.S. Pat. No. 4,795,751; JP Publication No. 89/100165; U.S. Pat. No. 4,730,000; *J. Med. Chem.*, 1986, 29, 2363–2369; and U.S. Pat. No. 4,777,253).

Potassium carbonate is commercially available in form of granules. However, when granular potassium carbonate is used in a reaction for cyclizing a quinoline-ring, the reaction cannot be completed and the yield is very low, about 20~30%. Therefore, in order to complete the reaction, granular forms of potassium carbonate need to be reduced to powder, which requires an additional process, excess amounts of potassium carbonate (about 3–5 eq.), and/or equipment for grinding the granules in a reactor. Further, when a reaction is performed in high temperature using potassium carbonate, carbon dioxide ($CO_2$) gas is produced, which makes the process dangerous. Accordingly, potassium carbonate has difficulties to be applied to an industrial-scale mass production.

Meanwhile, sodium hydride is very sensitive to water, which makes the reaction violent and dangerous (e.g., a possibility of explosion). Further, the yield thereof shows very high variation, about from 50 to 90%, so that it is also difficult to be applied to an industrial-scale mass production.

SUMMARY OF THE INVENTION

The present invention provides a process for preparing quinolonecarboxylate derivatives under a mild condition in a high yield, so as to be favorably applied to a large-scale mass production.

In one aspect of the present invention, there is provided a process for preparing a compound of formula (I) or its salt, which comprises reacting a compound of formula (II) with potassium phosphate tribasic ($K_3PO_4$) in an organic solvent:

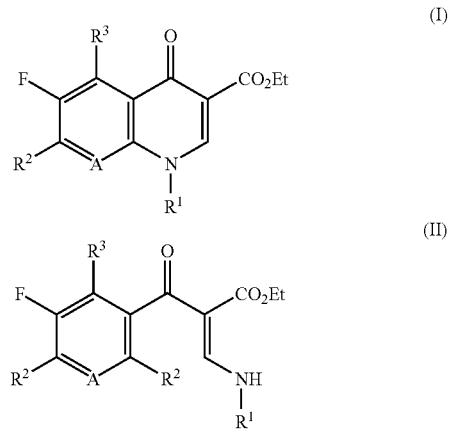

wherein, $R^1$ is cyclopropyl, 2,4-difluorophenyl, or 1-acetoxyprop-2(S)-yl; $R^2$ and $R^3$ are independently hydrogen, chloro, or fluoro; and A is CH, CF, $CNO_2$, or N.

The above and other features and advantages of the present invention will become more apparent by describing in detail a preferred embodiment thereof.

DETAILED DESCRIPTION OF THE INVENTION

In accordance with one aspect of the present invention, quinolonecarboxylate derivatives are prepared in high yield by reacting a compound of formula (II) with $K_3PO_4$ in an organic solvent. The resulting compound may be further purified and isolated. This process may be illustrated as the following reaction scheme 1.

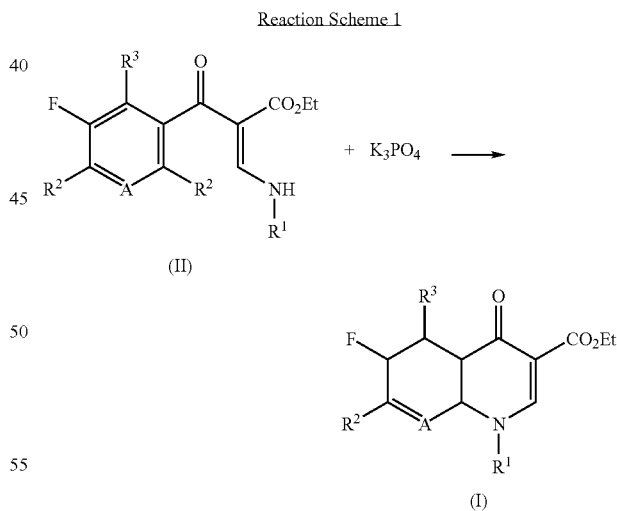

In the above reaction scheme 1, A, $R^1$, $R^2$, and $R^3$ are the same as defined above.

The compound of formula (II) may be prepared by a method which is known in the art (U.S. Pat. No. 5,237,060). For example, the compound of formula (II) may be prepared by reacting a compound of the following formula (III) with amine derivatives ($NH_2$—$R^1$) in an organic solvent such as dichloromethane, alcohol, chloroform, cyclohexane or toluene. The reaction may be performed at 20° C.~25° C.

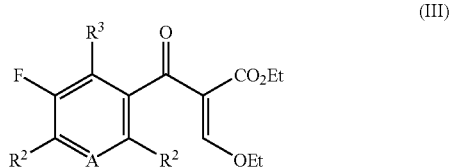
(III)

In the compound of formula (III), A, $R^2$ and $R^3$ are the same as defined above.

The compound of formula (III) may be prepared by a method which is known in the art (*J. Med. Chem.*, 1986, 29, 2363; *J. Org. Chem.*, 1970, 35, 930; *Organicum*, $3^{rd}$ edition, 1964, 438; and U.S. Pat. No. 5,237,060).

In the process of the present invention, potassium phosphate tribasic may be used in an excess amount, i.e., about 1.5~2.8 eq., preferably 1.5~2.0 eq. to 1 eq. of the compound of formula (II), so as to obtain the product in high yield. In case that potassium phosphate tribasic is used less than 1.5 eq. to 1 eq. of the compound of formula (II), the compound of formula (II) may remain un-reacted.

The process of the present invention may be performed in the presence of various organic solvents, including methyl alcohol, ethyl alcohol, isopropyl alcohol, methylene chloride, dichloroethane, chloroform, acetone, methyl ethyl ketone, ethyl acetate, methyl acetate, toluene, benzene, acetonitrile, N,N-dimethylformamide, N,N-dimethylacetamide, dimethylsulfoxide, and etc. Among them, a solovent useful for the present invention preferably includes acetonitrile methyl ethyl ketone, ethyl acetate, ethyl alcohol, dichloroethane and toluene, more preferably includes acetonitrile.

Although a higher temperature may increase a reaction rate, the reaction may be performed at 60° C.~82° C., preferably at 75° C.~80° C., to obtain the product in high purity and yield. The reaction may be performed in about 1~12 hours, preferably about 1~3 hours.

The process of the present invention may further comprise a step for purifying in order to remove any by-product, e.g., potassium phosphate dibasic. The purifying step may be performed according to conventional methods. For example, the reaction mixture obtained in the above is filtered, preferably under a reduced pressure. An organic solvent, such as dichloromethane, ethyl acetate, or a mixture thereof, is added to the concentrate of the resulting filtrate, followed by washing with water. The resulting organic layer is concentrated to obtain a purified product, i.e., the compound of formula (I).

By using potassium phosphate tribasic according to the present invention, quinolonecarboxylate derivatives of formula (I) can be prepared under a mild condition in high yield, so as to be favorably applied to a large-scale mass production thereof. Further, using 3-quinolonecarboxylate derivatives obtained according to the process of the present invention, various intermediates for the preparation of quinolone anti-bacterial agents, including sparfloxacin, gemifloxacin, trovafloxacin, ciprofloxacin, temafloxacin, fleroxacin, levofloxacin, or etc., can be favorably prepared under a mild condition in large-scale mass production.

The present invention is further illustrated and described by the following examples, which should not be taken to limit the scope of the invention.

EXAMPLE 1:

Preparation of ethyl 1-cyclopropyl-5,6,7,8-tetrafluoro-1,4-dihydro-4-oxoquinoline-3-carboxylate 3.0 g of ethyl 3-cyclopropylamino-2-pentafluorobenzoyl acrylate was dissolved in 15 ml of acetonitrile under heating to 75~80° C. 3.28 g (1.8 eq.) of $K_3PO_4$ was added in portions to the reaction mixture, which was then stirred at the same temperature for 1.5 hours. The reaction mixture was filtered under a reduced pressure and washed with 30 ml of dichloromethane. The filtrate was concentrated under a reduced pressure. The resulting residue was dissolved in 30 ml of dichloromethane and then washed with water. The organic layer was concentrated under a reduced pressure to give 2.74 g of ethyl 1-cyclopropyl-5,6,7,8-tetrafluoro-1,4-dihydro-4-oxoquinoline-3-carboxylate (Yield: 96.9%).

$^1$H NMR (CDCl$_3$, ppm): 1.17(4H, m, CH$_2$CH$_2$), 1.39(3H, t, J=8, CH$_2$CH$_3$), 3.88(1H, m, NCH), 4.37(2H, q, J=8, CH$_2$CH$_3$), 8.48(1H, s, C2-H)

EXAMPLE 2

Preparation of ethyl 7-chloro-1-cyclopropyl-6-fluoro-1,4-dihydro-4-oxo-1,8-naphthyridine-3-carboxylate 7.0 g of ethyl 3-cyclopropylamino-2-(2,6-dichloro-5-fluoropyridine-3-carbonyl)acrylate was dissolved in 35 ml of acetonitrile under heating to 75~80° C. 8.56 g (2.0 eq.) of $K_3PO_4$ was added in portions to the reaction mixture, which was then stirred at the same temperature for 1.5 hours. The reaction mixture was filtered under a reduced pressure and washed with 77 ml of dichloromethane. The filtrate was concentrated under a reduced pressure. The resulting residue was dissolved in 77 ml of dichloromethane and then washed with water. The organic layer was concentrated under a reduced pressure to give 6.17 g of ethyl 7-chloro-1-cyclopropyl-6-fluoro-1,4-dihydro-4-oxo-1,8-naphthyridine-3-carboxylate (Yield: 98.5%).

$^1$H NMR(CDCl$_3$, ppm): 1.20(4H, m, CH$_2$CH$_2$), 1.41(3H, t, J=8, CH$_2$CH$_3$), 3.66(1H, m, NCH), 4.41(2H, q, J=8, CH$_2$CH$_3$), 8.44(1H, d, J=4, C5-H), 8.66(1H, s, C2-H)

EXAMPLE 3

Preparation of ethyl 1-(2,4-difluorophenyl)-6,7-difluoro-1,4-dihydro-4-oxo-1,8-naphthyridine-3-carboxylate 6.0 g of ethyl 2-(2,6-dichloro-5-fluoropyridine-3-carbonyl)-3-(2,4-difluorophenylamino)acrylate was dissolved in 30 ml of acetonitrile under heating to 75~80° C. 5.47 g (1.8 eq.) of $K_3PO_4$ was added in portions to the reaction mixture, which was then stirred at the same temperature for 1.5 hours. The reaction mixture was filtered under a reduced pressure and washed with 66 ml of dichloromethane. The filtrate was concentrated under a reduced pressure. The resulting residue was dissolved in 66 ml of dichloromethane and then washed with water. The organic layer was concentrated under a reduced pressure to give 5.25 g of ethyl 1-(2,4-difluorophenyl)-6,7-difluoro-1,4-dihydro-4-oxo-1,8-naphthyridine-3-carboxylate (Yield: 95.8%).

$^1$H NMR(CDCl$_3$, ppm): 1.41(3H, t, J=8, CH$_2$CH$_3$), 4.41 (2H, q, J=8, CH$_2$CH$_3$), 7.12(2H, m, aromatic C5'-& C6'-H), 7.45(1H, m, aromatic C3'-H), 8.48(1H, d, J=8, C5-H), 8.55(1H, s, C2-H)

EXAMPLE 4

Preparation of ethyl 1-cyclopropyl-6,7-difluoro-1,4-dihydro-4-oxoquinoline-3-carboxylate 10.0 g of ethyl 2-(2-chloro-4,5-difluorobenzoyl-3-cyclopropylamino)acrylate was dissolved in 50 ml of acetonitrile under heating to 75~80° C. 18.03 g (2.8 eq.) of $K_3PO_4$ was added in portions to the reaction mixture, which was then stirred at the same temperature for 2 hours. The reaction mixture was filtered under a reduced pressure and washed with 60 ml of dichloromethane. The filtrate was concentrated under a reduced pressure. The resulting residue was dissolved in 300 ml of dichloromethane and then washed with water. The organic layer was concentrated under a reduced pressure to give 8.77 g of ethyl 1-cyclopropyl-6,7-difluoro-1,4-dihydro-4-oxoquinoline-3-carboxylate (Yield: 98.7%).

$^1$H NMR(CDCl$_3$, ppm): 1.26(4H, m, CH$_2$CH$_2$), 1.41(3H, t, J=8, CH$_2$CH$_3$), 3.44(1H, m, NCH), 4.39(2H, q, J=8, CH$_2$CH$_3$), 7.73(1H, m, C8-H), 8.25(1H, m, C5-H), 8.58(1H, s, C2-H)

EXAMPLE 5

Preparation of ethyl 1-(2,4-difluorophenyl)-6,7-difluoro-1,4-dihydro-4-oxoquinoline-3-carboxylate 8.0 g of ethyl 2-(2-chloro-4,5-difluorobenzoyl)-3-(2,4-difluorophenylamino)acrylate was dissolved in 80 ml of acetonitrile under heating to 75~80° C. 11.84 g (2.8 eq.) of $K_3PO_4$ was added in portions to the reaction mixture, which was then stirred at the same temperature for 2 hours. The reaction mixture was filtered under a reduced pressure and washed with 40 ml of dichloromethane. The filtrate was concentrated under a reduced pressure. The resulting residue was dissolved in 88 ml of dichloromethane and then washed with water. The organic layer was concentrated under a reduced pressure to give 6.69 g of ethyl 1-(2,4-difluorophenyl)-6,7-difluoro-1,4-dihydro-4-oxoquinoline-3-carboxylate (Yield: 92%).

$^1$H NMR(CDCl$_3$, ppm): 1.40(3H, t, J=8, CH$_2$CH$_3$), 4.39 (2H, q, J=8, CH$_2$CH$_3$), 6.67(1H, m, C8-H), 7.20(2H, m, aromatic C5'- & C6'-H), 7.54(1H, m, aromatic C3'-H), 8.29(1H, d, J=8, C5-H), 8.38(1H, s, C2-H)

EXAMPLE 6

Preparation of ethyl 6,7,8-trifluoro-1-(2-fluoroethyl)-1,4-dihydro-4-oxoquinoline-3-carboxylate 8.0 g of ethyl 3-(2-fluoroethylamino)-2-(2,3,4,5-tetrafluorobenzoyl)acrylate was dissolved in 64 ml of acetonitrile under heating to 75~80° C. 9.06 g (1.8 eq.) of $K_3PO_4$ was added in portions to the reaction mixture, which was then stirred at the same temperature for 1.5 hours. The reaction mixture was filtered under a reduced pressure and washed with 80 ml of dichloromethane. The filtrate was concentrated under a reduced pressure. The resulting residue was dissolved in 48 ml of dichloromethane and then washed with water. The organic layer was concentrated under a reduced pressure to give 7.29 g of ethyl 6,7,8-trifluoro-1-(2-fluoroethyl)-1,4-dihydro-4-oxoquinoline-3-carboxylate (Yield: 96.9%).

$^1$H NMR(CDCl$_3$, ppm): 1.41(3H, t, J=8, CH$_2$CH$_3$), 4.40 (2H, q, J=8, CH$_2$CH$_3$), 4.60–4.89(4H, m, CH$_2$CH$_2$F), 8.20 (1H, m, C5-H), 8.39(1H, s, C2-H)

EXAMPLE 7

Preparation of (−) ethyl N-(acetoxy-prop-2(S)-yl)-6-fluoro-7-chloro-8-nitro-4-quinolone-3-carboxylate 3.0 g of (+) ethyl 2-(2,4-dichloro-3-nitro-5-fluorobenzoyl)-3-[(1-acetoxyprop-2(S)-yl)amino]acrylate was dissolved in 15 ml of acetonitrile under heating to 75~80° C. 2.12 g (1.5 eq.) of $K_3PO_4$ was added in portions to the reaction mixture, which was then stirred at the same temperature for 1.5 hours. The reaction mixture was filtered under a reduced pressure and washed with 60 ml of dichloromethane. The filtrate was concentrated under a reduced pressure. The resulting residue was dissolved in 50 ml of dichloromethane and then washed with water. The organic layer was concentrated under a reduced pressure to give 2.64 g of (−) ethyl N-(acetoxy-prop-2(S)-yl)-6-fluoro-7-chloro-8-nitro-4-quinolone-3-carboxylate (Yield: 95.7%)

$^1$H NMR(CDCl$_3$, ppm): 1.43 (3H, t, J=7.2, CH$_2$CH$_3$), 1.62(3H, d, J=6.8, NCHCH$_3$), 1.94(s, 3H), 4.13(1H, m, CH$_2$OAc), 4.31(1H, m, CH$_2$OAc), 4.43(3H, m, CH$_2$CH$_3$ & NCHCH$_3$), 8.45(1H, d, J=8.4, C5-H), 8.61 (1H, s, C2-H)

EXAMPLE 8

Preparation of (−) ethyl N-(acetoxy-prop-2(S)-yl)-6-fluoro-7-chloro-8-nitro-4-quinolone-3-carboxylate 45.69 g of (+) ethyl 2-(2,4-dichloro-3-nitro-5-fluorobenzoyl)-3-[(1-acetoxyprop-2(S)-yl)amino]acrylate was dissolved in 270 ml of acetonitrile under heating to 70~75° C. 32.25 g (1.5 eq.) of $K_3PO_4$ was added in portions to the reaction mixture, which was then stirred at the same temperature for 4 hours. The reaction mixture was filtered under a reduced pressure and washed with 500 ml of dichloromethane. The filtrate was concentrated under a reduced pressure. The resulting residue was dissolved in 300 ml of dichloromethane and then washed with water. The organic layer was concentrated under a reduced pressure to give 46.2 g of (−) ethyl N-(acetoxy-prop-2(S)-yl)-6-fluoro-7-chloro-8-nitro-4-quinolone-3-carboxylate (Yield: 95.4%).

EXAMPLE 9

Preparation of (−) ethyl N-(acetoxy-prop-2(S)-yl)-6-fluoro-7-chloro-8-nitro-4-quinolone-3-carboxylate 45.69 g of (+) ethyl 2-(2,4-dichloro-3-nitro-5-fluorobenzoyl)-3-[(1-acetoxyprop-2(S)-yl)amino]acrylate was dissolved in 270 ml of acetonitrile under heating to 65~70° C. 32.25 g (1.5 eq.) of $K_3PO_4$ was added in portions to the reaction mixture, which was then stirred at the same temperature for 4 hours. The reaction mixture was filtered under a reduced pressure and washed with 500 ml of dichloromethane. The filtrate was concentrated under a reduced pressure. The resulting residue was dissolved in 300 ml of dichloromethane and then washed with water. The organic layer was concentrated under a reduced pressure to give 45.4 g of (−) ethyl N-(acetoxy-prop-2(S)-yl )-6-fluoro-7-chloro-8-nitro-4-quinolone-3-carboxylate (Yield: 93.7%).

EXAMPLE 10

Preparation of (−) ethyl N-(acetoxy-prop-2(S)-yl)-6-fluoro-7-chloro-8-nitro-4-quinolone-3-carboxylate 45.69 g of (+) ethyl 2-(2,4-dichloro-3-nitro-5-fluorobenzoyl)-3-[(1-acetoxyprop-2(S)-yl)amino]acrylate was dissolved in 270 ml of acetonitrile under heating to 78~82° C. 32.25 g (1.5 eq.) of $K_3PO_4$ was added in portions to the reaction mixture, which was then stirred at the same temperature for 1.5 hours. The reaction mixture was filtered under a reduced pressure and washed with 500 ml of dichloromethane. The filtrate was concentrated under a reduced pressure. The resulting residue was dissolved in 300 ml of dichloromethane and then washed with water. The organic layer was concentrated under a reduced pressure to give 46.0 g of (−) ethyl N-(acetoxy-prop-2(S)-yl)-6-fluoro-7-chloro-8-nitro-4-quinolone-3-carboxylate (Yield: 95.0%).

EXAMPLE 11

Preparation of (−) ethyl N-(acetoxy-prop-2(S)-yl)-6-fluoro-7-chloro-8-nitro-4-quinolone-3-carboxylate 45.69 g of (+) ethyl 2-(2,4-dichloro-3-nitro-5-fluorobenzoyl)-3-[(1-acetoxyprop-2(S)-yl)amino]acrylate was dissolved in 270 ml of acetonitrile under heating to 70~75° C. 32.25 g (1.5 eq.) of $K_3PO_4$ was added in portions to the reaction mixture, which was then stirred at the same temperature for 12 hours. The reaction mixture was filtered under a reduced pressure and washed with 500 ml of dichloromethane. The filtrate was concentrated under a reduced pressure. The resulting residue was dissolved in 300 ml of dichloromethane and then washed with water. The organic layer was concentrated under a reduced pressure to give 46.6 g of (−) ethyl N-(acetoxy-prop-2(S)-yl)-6-fluoro-7-chloro-8-nitro-4-quinolone-3-carboxylate (Yield: 96.1%).

EXAMPLE 12

Preparation of ethyl 6,7,8-trifluoro-1-(2-fluoroethyl)-1,4-dihydro-4-oxoquinoline-3-carboxylate 1.0 g of ethyl 3-(2-fluoroethylamino)-2-(2,3,4,5-tetrafluorobenzoyl)acrylate was dissolved in 8 ml of methyl ethyl ketone under heating to 75~80° C. 1.14 g (1.8 eq.) of $K_3PO_4$ was added in portions to the reaction mixture, which was then stirred at the same temperature for 1.5 hours. The reaction mixture was filtered under a reduced pressure and washed with 40 ml of dichloromethane. The filtrate was concentrated under a reduced pressure. The resulting residue was dissolved in 20 ml of dichloromethane and then washed with water. The organic layer was concentrated under a reduced pressure to give 0.91 g of ethyl 6,7,8-trifluoro-1-(2-fluoroethyl)-1,4-dihydro-4-oxoquinoline-3-carboxylate (Yield: 96.8%).

EXAMPLE 13

Preparation of ethyl 6,7,8-trifluoro-1-(2-fluoroethyl)-1,4-dihydro-4-oxoquinoline-3-carboxylate 1.0 g of ethyl 3-(2-fluoroethylamino)-2-(2,3,4,5-tetrafluorobenzoyl) acrylate was dissolved in 8 ml of ethyl acetate under heating to 70~75° C. 1.14 g (1.8 eq.) of $K_3PO_4$ was added in portions to the reaction mixture, which was then stirred at the same temperature for 1.5 hours. The reaction mixture was filtered under a reduced pressure and washed with 40 ml of dichloromethane. The filtrate was concentrated under a reduced pressure. The resulting residue was dissolved in 20 ml of dichloromethane and then washed with water. The organic layer was concentrated under a reduced pressure to give 0.9 g of ethyl 6,7,8-trifluoro-1-(2-fluoroethyl)-1,4-dihydro-4-oxoquinoline-3-carboxylate (Yield: 95.7%).

EXAMPLE 14

Preparation of ethyl 6,7,8-trifluoro-1-(2-fluoroethyl)-1,4-dihydro-4-oxoquinoline-3-carboxylate 1.0 g of ethyl 3-(2-fluoroethylamino)-2-(2,3,4,5-tetrafluorobenzoyl) acrylate was dissolved in 8 ml of EtOH under heating to 70~75° C. 1.14 g (1.8 eq.) of $K_3PO_4$ was added in portions to the reaction mixture, which was then stirred at the same temperature for 1.5 hours. The reaction mixture was filtered under a reduced pressure and washed with 40 ml of dichloromethane. The filtrate was concentrated under a reduced pressure. The resulting residue was dissolved in 20 ml of dichloromethane and then washed with water. The organic layer was concentrated under a reduced pressure to give 0.9 g of ethyl 6,7,8-trifluoro-1-(2-fluoroethyl)-1,4-dihydro-4-oxoquinoline-3-carboxylate (Yield: 95.7%).

EXAMPLE 15

Preparation of ethyl 6,7,8-trifluoro-1-(2-fluoroethyl)-1,4-dihydro-4-oxoquinoline-3-carboxylate 1.0 g of ethyl 3-(2-fluoroethylamino)-2-(2,3,4,5-tetrafluorobenzoyl) acrylate was dissolved in 8 ml of 1,2-dichloroethane under heating to 75~80° C. 1.14 g (1.8 eq.) of $K_3PO_4$ was added in portions to the reaction mixture, which was then stirred at the same temperature for 3.0 hours. The reaction mixture was filtered under a reduced pressure and washed with 40 ml of dichloromethane. The filtrate was concentrated under a reduced pressure. The resulting residue was dissolved in 20 ml of dichloromethane and then washed with water. The organic layer was concentrated under a reduced pressure to give 0.89 g of ethyl 6,7,8-trifluoro-1-(2-fluoroethyl )-1,4-dihydro-4-oxoquinoline-3-carboxylate (Yield: 94.7%).

EXAMPLE 16

Preparation of ethyl 6,7,8-trifluoro-1-(2-fluoroethyl)-1,4-dihydro-4-oxoquinoline-3-carboxylate 1.0 g of ethyl 3-(2-fluoroethylamino)-2-(2,3,4,5-tetrafluorobenzoyl) acrylate was dissolved in 8 ml of toluene under heating to 75~80° C. 1.14 g (1.8 eq.) of $K_3PO_4$ was added in portions to the reaction mixture, which was then stirred at the same temperature for 6.0 hours. The reaction mixture was filtered under a reduced pressure and washed with 40 ml of dichloromethane. The filtrate was concentrated under a reduced pressure. The resulting residue was dissolved in 20 ml of dichloromethane and then washed with water. The organic layer was concentrated under a reduced pressure to give 0.89 g of ethyl 6,7,8-trifluoro-1-(2-fluoroethyl)-1,4-dihydro-4-oxoquinoline-3-carboxylate (Yield: 94.7%).

COMPARATIVE EXAMPLE 1

Preparation of ethyl 1-cyclopropyl-5,6,7,8-tetrafluoro-1,4-dihydro-4-oxoquinoline-3-carboxylate 3.0 g of ethyl 3-cyclopropylamino-2-pentafluorobenzoyl acrylate and 3.66 g (3.1 eq.) of anhydrous potassium carbonate were added to 22.2 ml of N,N-dimethylformamide. The reaction mixture was stirred for 18 hours at room temperature. The reaction mixture was concentrated under a reduced pressure to remove the solvent. 60 ml of dichloromethane was added to the resulting residue, which was then washed twice with 50 ml of water. The organic layer was dried over $MgSO_4$ and filtered under a reduced pressure. The resulting filtrate is concentrated under a reduced pressure to give 2.59 g of ethyl 1-cyclopropyl-5,6,7,8-tetrafluoro-1,4-dihydro-4-oxoquinoline-3-carboxylate (Yield: 91.5%).

COMPARATIVE EXAMPLE 2

Preparation of ethyl 1-cyclopropyl-5,6,7,8-tetrafluoro-1,4-dihydro-4-oxoquinoline-3-carboxylate The solution of 3.0 g of ethyl 3-cyclopropylamino-2-pentafluorobenzoyl acrylate in 36.4 ml of anhydrous tetrahydrofuran was cooled to 10° C. 0.41 g of 60% sodium hydride was added to the reaction mixture, which was then stirred for 18 hours at room temperature. The reaction mixture was cooled to 5~10° C. 36.4 ml of water is added to the reaction mixture, which was then stirred for 30 minutes. The organic layer was filtered under a reduced pressure and washed with water. The resulting wet cake was dried under a reduced pressure at 50° C. for 5 hours to give 2.01 g of ethyl 1-cyclopropyl-5,6,7,8-tetrafluoro-1,4-dihydro-4-oxoquinoline-3-carboxylate (Yield: 71%).

COMPARATIVE EXAMPLE 3

Preparation of ethyl 7-chloro-1-cyclopropyl-6-fluoro-1,4-dihydro-4-oxo-1,8-naphthyridine-3-carboxylate The solution of 3.0 g of ethyl 3-cyclopropylamino-2-(2,6-dichloro-5-fluoropyridine-3-carbonyl)acrylate in 36.4 ml of anhydrous tetrahydrofuran was cooled to 10° C. 0.36 g (1.05 eq.) of 60% sodium hydride was added to the reaction mixture, which was then stirred for 18 hours at room temperature. The reaction mixture was cooled to 5~10° C. 36.4 ml of water was added to the reaction mixture, which was then stirred for 30 minutes. The organic layer was filtered under a reduced pressure and washed with water. The resulting wet cake was dried under a reduced pressure at 50° C. for 5 hours to give 2.34 g of ethyl 7-chloro-1-cyclopropyl-6-fluoro-1,4-dihydro-4-oxo-1,8-naphthyridine-3-carboxylate (Yield: 87.3%).

COMPARATIVE EXAMPLE 4

Preparation of ethyl 1-(2,4-difluorophenyl)-6,7-difluoro-1,4-dihydro-4-oxo-1,8-naphthyridine-3-carboxylate The solution of 3.0 g of ethyl 2-(2,6-dichloro-5-fluoropyridine-3-carbonyl)-3-(2,4-difluorophenylamino)acrylate in 36.4 ml of anhydrous tetrahydrofuran was cooled to 10° C. 0.3 g (1.05 eq.) of 60% sodium hydride was added to the reaction mixture, which was refluxed for 1 hour under $N_2$ gas. The reaction mixture was cooled to 5~10° C. 36.4 ml of water was added to the reaction mixture, which was then stirred for 30 minutes. The organic layer was filtered under a reduced pressure and washed with water. The resulting wet cake was dried under a reduced pressure at 50° C. for 5 hours to give 2.33 g of ethyl 1-(2,4-difluorophenyl)-6,7-difluoro-1,4-dihydro-4-oxo-1,8-naphthyridine-3-carboxylate (Yield: 82.0%).

COMPARATIVE EXAMPLE 5

Preparation of ethyl 1-cyclopropyl-6,7-difluoro-1,4-dihydro-4-oxoquinoline-3-carboxylate The solution of 3.0 g of ethyl 2-(2-chloro-4,5-difluorobenzoyl)-3-cyclopropylamino acrylate in 12 ml of 1,2-dimethyl-2-imidazolidinone was heated to 100~120° C. 1.76 g (1.4 eq.) of potassium carbonate was added to the reaction mixture, which was refluxed for 4 hours. The reaction was not completed (confirmed by TLC check).

COMPARATIVE EXAMPLE 6

Preparation of ethyl 1-(2,4-difluorophenyl)-6,7-difluoro-1,4-dihydro-4-oxoquinoline-3-carboxylate The solution of 3.0 g of ethyl 2-(2-chloro-4,5-difluorobenzoyl)-3-(2,4-difluorophenylamino)acrylate in 30 ml of anhydrous tetrahydrofuran was cooled to 10° C. 0.3 g (1.02 eq.) of 60% sodium hydride was added to the reaction mixture, which was refluxed for 4.5 hours. The reaction mixture was cooled to 5~10° C. 54.6 ml of water was added to the reaction mixture, which was then stirred for 30 minutes. The organic layer was filtered under a reduced pressure and washed with a mixed solution of n-hexane and ether (1/1). The resulting wet cake was dried under a reduced pressure at 40~45° C. for 6 hours to give 2.26 g of ethyl 1-(2,4-difluorophenyl)-6,7-difluoro-1,4-dihydro-4-oxoquinoline-3-carboxylate (Yield: 82.8%).

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A process for preparing a compound of formula (I) or its salt, which comprises reacting a compound of formula (II) with potassium phosphate tribasic ($K_3PO_4$) in an organic solvent:

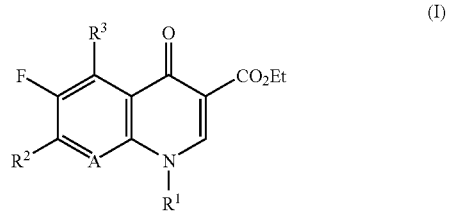

-continued

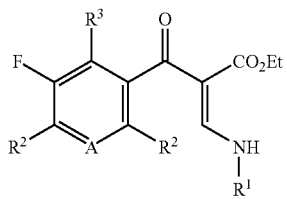

(II)

wherein, R1 is cyclopropyl, 2,4-difluorophenyl, 2-fluoroethyl, or 1-acetoxyprop-2(S)-yl; R2 and R3 are independently hydrogen, chloro, or fluoro; and A is CH, CF, CNO2, or N.

2. The process of claim 1, wherein the organic solvent is selected from the group consisting of acetonitrile, methyl ethyl ketone, ethyl acetate, ethyl alcohol, dichloroethane, and toluene.

3. The process of claim 1, wherein amount of the potassium phosphate tribasic is 1.5 eq.~2.8 eq. to 1 eq. of the compound of formula (II).

4. The process of claim 1, wherein the reacting is carried out at 60° C.~85° C.

5. The process of claim 4, wherein the reacting is carried out at 75° C.~80° C.

6. The process of claim 1, wherein the reacting is completed in about 1~12 hours.

7. The process of claim 6, wherein the reacting is completed in about 1~3 hours.

8. The process of claim 1, further comprising a purifying step which comprises filtering a resulting product obtained from the process of any one of claims 1 through 7 to remove any by-product; concentrating the resulting filtrate; adding an organic solvent to the concentrate, followed by washing with water; and concentrating the resulting organic layer.

9. The process of claims 8, wherein the organic solvent is dichloromethane, ethyl acetate, or a mixture thereof.

* * * * *